United States Patent [19]

Sandlin et al.

[11] 4,398,543

[45] Aug. 16, 1983

[54] MOISTURE COLLECTING CHAMBER

[76] Inventors: Felix M. Sandlin, 420 Tower Dr., San Antonio, Tex. 78232; Richard L. De Villez, 10 River Oaks Dr., New Braunfels, Tex. 78130; Jack D. Waller, 2406 Lipscomb, Amarillo, Tex. 79109

[21] Appl. No.: 233,565

[22] Filed: Feb. 11, 1981

[51] Int. Cl.³ .............................................. A61B 19/00
[52] U.S. Cl. ..................................... 128/760; 73/73; 73/335; 73/338; 128/749
[58] Field of Search .................... 128/630, 749; 73/73, 73/335–336, 338

[56] References Cited

U.S. PATENT DOCUMENTS

| 3,139,085 | 6/1964 | Custance et al. | 128/630 |
| 3,241,431 | 3/1966 | Brutten et al. | 128/630 |
| 3,318,302 | 5/1967 | Adams | 128/630 |
| 4,066,068 | 1/1978 | Nilsson et al. | 128/630 |
| 4,266,556 | 5/1981 | Barlow et al. | 128/630 |

Primary Examiner—George F. Lesmes
Assistant Examiner—Nancy A. B. Swisher
Attorney, Agent, or Firm—Cox & Smith Incorporated

[57] ABSTRACT

A moisture collecting chamber apparatus for testing skin by passing a standard gas over the skin area to be tested including a probe which engages the skin surface and a limit means to limit the engagement of the probe with the skin surface and provide a seal.

1 Claim, 4 Drawing Figures

MOISTURE COLLECTING CHAMBER

BACKGROUND OF THE INVENTION

This invention relates generally to determining transepidermal water loss from the skin. More particularly, the invention relates to a moisture dermatometer that is device for measuring the moisture content of human skin (the stratum corneum). For cosmetic and medical purposes, it is desirable to be able to measure the moisture in the skin. Two known methods for performing this are shown in U.S. Pat. Nos. 4,013,065 and 4,066,068. Other U.S. patents relating to skin testing in one form or another are U.S. Pat. Nos. 2,318,207; 3,635,213; and 4,195,641.

It is also known that skin moisture can be tested by passing a dry gas over the skin and then through an electrolytic sensor determining the amount of moisture picked up by the dry gas. The typical type of gas which might be used in this situation would be dry nitrogen which would be passed over a small skin area. Various sensors or moisture collecting chambers have heretofore been utlized to pass dry gas over the skin area.

A problem which arises when passing the dry gas over the skin area is providing an accurate measurement. The dry gas must be passed over a predetermined skin area for a predetermined amount of time to provide a standard sample. As far as known, this requires handholding a collector over the skin area. One of the problems with holding the collector over the skin area is providing uniform pressure for the predetermined amount of time to provide the uniform results without discomfort to the patient. The collector must also form a seal with the area being tested to provide uniform results. It is an object of this invention to overcome these problems in the prior art and provide a device which will provide uniform and accurate results and which can be easily used by any technician.

SUMMARY OF THE INVENTION

A moisture collecting chamber having a probe which engages the skin to form a seal between the probe and the skin surface which is being tested and to provide a substantially uniform force when the probe is positioned on a patient. A connecting mechanism is attached to the probe and limiting means is mounted with the probe to provide uniform pressure of the probe against the skin surface during each test.

BRIEF DESCRIPTION OF THE PREFERRED EMBODIMENT

Figure 1:
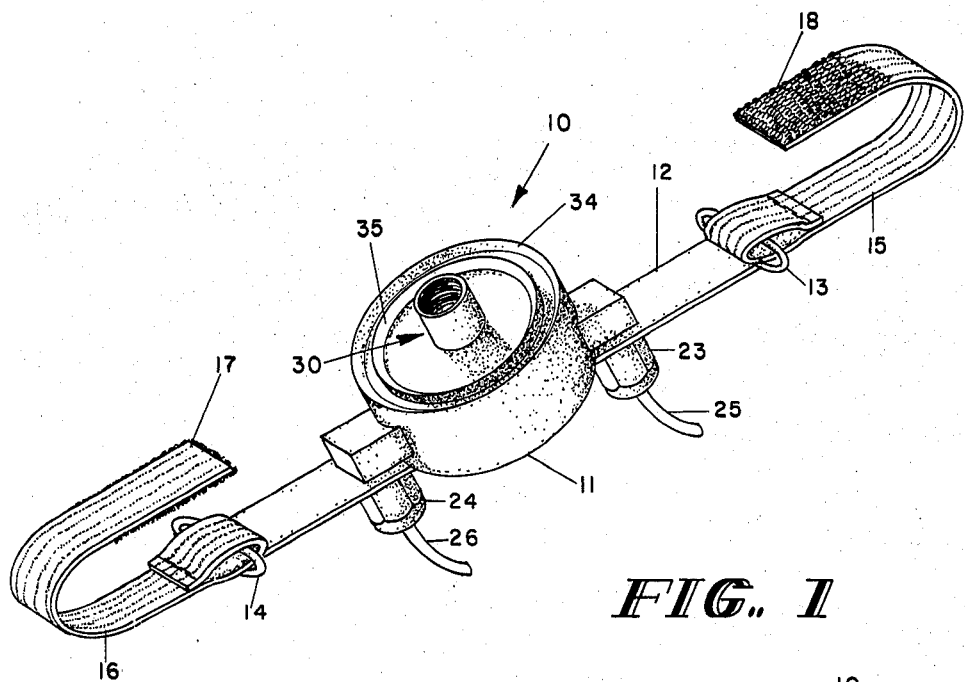
FIG. 1 is a perspective view of the moisture collecting chamber of the invention.

Referring to FIG. 1 of the invention, there is shown a moisture collecting chamber apparatus 10. The apparatus includes a cylindrical housing 11 to which is attached a connecting device or stabilizing bar 12. The connecting device 12 includes loops 13 and 14 which are connected at opposite ends of the connecting device or bar 12. Straps 15 and 16 are connected to the loops 13 and 14 respectively for wrapping around the appendage of a patient such as the forearm. The straps 15 and 16 include hook means 17 and pile means 18 as a fastening means which may be interconnected to hold the apparatus on a patient. The hook and pile fastener allow for uniform connection to any size appendage. The connecting device or bar 12 extends outwardly past the housing 11 at opposite sides thereof so that the straps 15 and 16 do not engage the appendage of the patient around its entire circumference. This helps prevent cutting off of circulation and discomfort to the patient. It also facilitates attachment of the apparatus to persons having varying sized appendages.

Figure 2:
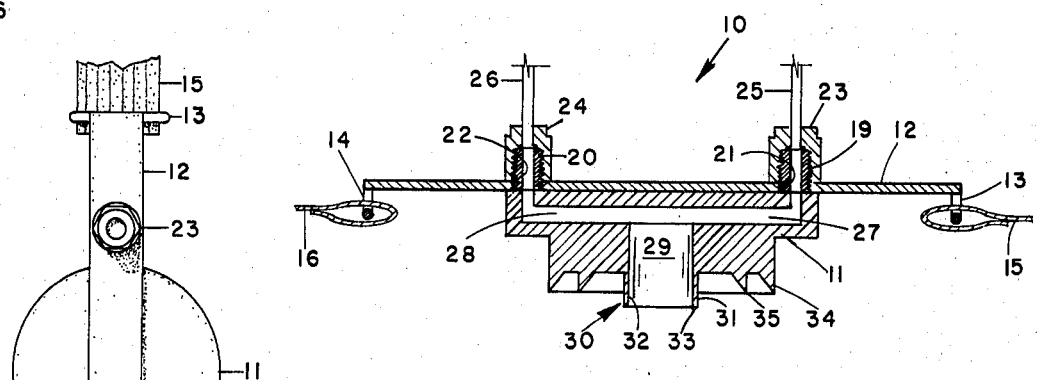
FIG. 2 is a cross-sectional view of the moisture collecting chamber.
Figure 4:
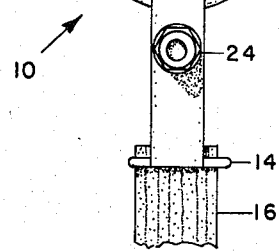
FIG. 4 is a top view of the moisture collecting chamber.

The housing 11 includes threaded connectors 19 and 20 as best shown in FIG. 2 which extend through openings 21 and 22 respectively in the connecting device 12. Suitable nuts 23 and 24 connect with the threaded connectors 19 and 20 respectively. The nuts 23 and 24 connect with lines 25 and 26 which are connected to a known electrolytic moisture analyzer (not shown).

The housing 11 as shown in FIG. 2 includes a channel or conduit 27 which connects with line 25. The housing 11 also includes a second channel or conduit 28 which connects with line 26. The channels 27 and 28 converge to a central opening 29 which connects to a probe 30. The probe 30 is defined by an outer surface 31, inner surface 32 and an end sealing surface 33.

The housing 11 further includes cylindrical engaging or limiting means 34 and 35 which are adapted to engage the skin surface of a patient. As will be apparent, the engaging means 34 and 35 surround the probe 30 and further act to form a seal.

Figure 3:
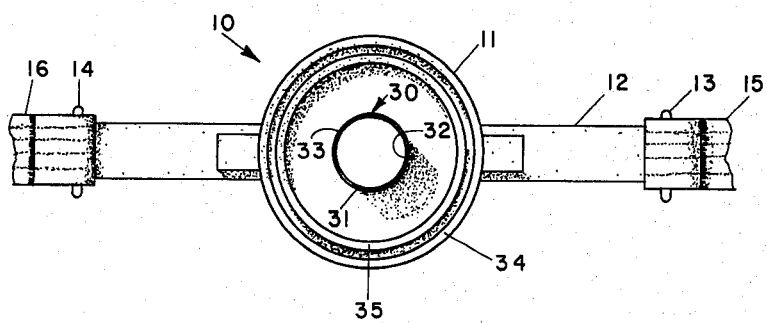
FIG. 3 is a bottom view of the moisture collecting chamber.

The housing 11 has a aperture of about 1.5 inches, a circumference of about 4.71 inches and an area of about 1.75 square inches. The connecting device 12 has a length of about 4 inches, a width of about 0.5 inches and is about 0.0625 inches thick. Referring to FIGS. 2 and 3, the opening defined by the inner surface 32 has a diameter of approximately 0.4357 inches. The outer diameter of the probe 30 as defined by the outer surface 31 is approximately 0.46875 inches. Engaging means 35 has a diameter of about 1 inch and the engaging means 34 has a diameter of approximately 1.5 inches. The surface 33 of the probe extends below the lower most point of the engaging means 34 and 35.

In operation, the moisture collecting chamber apparatus 10 is positioned against the forearm or similar appendage of a patient and the straps 15 and 16 are looped around the appendage so that the hook and pile fasteners 17 and 18 may be connected. This holds the apparatus on the patient in a comfortable position and maintains uniform pressure. The end surface 33 of the probe 30 extends below the lower most point of the limiting or engaging means 34 and 35 to provide the uniform pressure whenever the device is attached to a patient. The limit or engaging means 34 and 35 are generally triangular in cross-section and include edges which have pointed ends. The shape of the engaging means helps provide a seal. These pointed ends will cause discomfort if the apparatus is pressed too hardly against the appendage being tested. This enables the technician to place the apparatus on an appendage so that it is sealingly positioned against the appendage with uniform pressure but without too much discomfort to the patient. The pointed edges as well as the surface 33 form seals to prevent escape of the dry gas.

The dry gas is directed through the line 25 so that it passes through the channel 27 and comes in contact with the skin engaging the opening defined by the surface 32. The dry gas will pick up moisture from the skin depending on the moisture content of the skin and the gas will then pass through the conduit 28 and out the line 26. Lines 25 and 26 are connected to a standard moisture tester which is capable of measuring the moisture added to the standard dry gas.

The device can be attached to any patient by an untrained technician since the engaging means and length of the probe 30 provide a uniform pressure against the skin surface. This provides uniform data for each test which provides more accurate measurement of the moisture content. The connecting device 12 and straps 15 and 16 can be easily attached to provide relatively uniform pressure each time the device is attached to any appendage. This provides a uniform sample and allows the device to be positioned on the appendage and held there for the required amount of time without too much discomfort of the patient. It is not necessary for the patient or a technician to hold the device against the appendage and try to maintain constant pressure to provide uniform and standard test results.

Although the invention has been described in conjunction with the foregoing specific embodiment, many alternatives, variations and modifications are apparent to those of ordinary skill in the art. Those alternatives, variations and modifications are intended to fall within the spirit and scope of the appended claim.

I claim:

1. An apparatus for use with a device for testing skin moisture by passing a gas having a known moisture content over the skin area to be tested to pick up the moisture in the skin, comprising:
    a housing for attaching to the skin surface to be tested;
    a cylindrical probe on the housing for sealingly engaging the skin surface to be tested;
    a gas inlet and a gas outlet means in fluid communication with the enclosed volume of said cylindrical probe;
    a limit means on the housing for engaging the skin surface adjacent the area to be tested;
    said limit means including a plurality of concentric rings having a generally triangular cross-section; and
    said probe extending a predetermined distance past the limit means to provide a sufficient seal between the probe and skin to be tested when the probe is pressed against the skin area to engage the skin at a deeper level than the engagement made by the concentric rings of the limit means when they engage the skin surface so that the apparatus is uniformly positioned on any user to provide accurate test results.

* * * * *